United States Patent
Struble et al.

(10) Patent No.: US 7,069,079 B2
(45) Date of Patent: Jun. 27, 2006

(54) PRESSURE REGULATED ATRIO-VENTRICULAR DELAY FOR MULTI-SITE PACING

(75) Inventors: Chester L. Struble, Eijsden (NL); Pierre A. Grandjean, Warsage (BE)

(73) Assignee: Medtronic, Inc., Minneapolis, MN (US)

( * ) Notice: Subject to any disclaimer, the term of this patent is extended or adjusted under 35 U.S.C. 154(b) by 404 days.

(21) Appl. No.: 10/422,702

(22) Filed: Apr. 24, 2003

(65) Prior Publication Data

US 2004/0215266 A1    Oct. 28, 2004

Related U.S. Application Data

(63) Continuation-in-part of application No. 10/360,765, filed on Nov. 29, 2001, now abandoned.

(51) Int. Cl.
*A61N 1/362* (2006.01)
(52) U.S. Cl. .................................................. 607/23
(58) Field of Classification Search ............... 607/4–32
See application file for complete search history.

(56) References Cited

U.S. PATENT DOCUMENTS

2005/0027322 A1*    2/2005    Warkentin .................... 607/17

\* cited by examiner

*Primary Examiner*—Scott M. Getzow
(74) *Attorney, Agent, or Firm*—Daniel G. Chapik; Girma Wolde-Michael; Paul H. McDowall

(57) ABSTRACT

The hemodynamic operation of certain heart disease patient can be improved using pressure regulated atrio-ventricular delay. The pressure regulated atrio-ventricular delay involves recording atrial activation and ventricle activation, identifying a maximum diastolic pressure, identifying a declination pressure, calculating a percent decrease, and adjusting atrio-ventricular delay. The declination pressure occurs at the beginning of an isovolumetric contraction. The percent decrease is calculated between the maximum diastolic pressure and the declination pressure. The atrio-ventricular delay is adjusted according to the percent decrease between the maximum diastolic pressure and the declination pressure.

2 Claims, 8 Drawing Sheets

PRESSURE REGULATED ATRIO-VENTRICULAR DELAY FOR MULTI-SITE PACING

RELATED APPLICATION

This is a continuation-in-part of U.S. Application No. 60/333,762, filed Nov. 29, 2001, that has been converted to a nonprovisional application Ser. No. 10/360,765, filed Nov. 29, 2001 now abandoned.

FIELD OF THE INVENTION

This disclosure relates to multi-site cardiac pacing and more particularly to timing between different pacing sites.

BACKGROUND OF THE INVENTION

Heart failure is a lifelong condition that affects approximately 5 million people in the United States. Heart failure patients with dilated cardiomyopathy and combined conduction defects such as $1^{st}$ atrio-ventricular block, left bundle branch block (LBBB), right blundle branch block (RBBB) or intraventricular conduction defects (IVCD) typically demonstrate significant asynchrony between right-ventricle and left-ventricle contraction patterns. The right-ventricle and left-ventricle asynchrony represents a mismatch between right atrio-ventricular and left atrio-ventricular timing indices. The mismatched timing indices typically leads to poor ventricular filling, fusion of atrio-ventricular valve flow characteristics (fusion of E and A waves), increased potential of mitral or tricuspid blood flow regurgitation, and hemodynamic deterioration.

Previous drug treatments for heart failure

Previous multi-site pacing therapies for heart failure involve left-ventricular pacing or bi-ventricular pacing.

For the foregoing reasons, a new approach to regulating atrio-ventricular delay for multi-site pacing is needed.

BRIEF SUMMARY OF THE INVENTION

The pressure regulated atrio-ventricular delay for multi-site pacing improves heart hemodynamic for patients with certain forms of heart disease. The pressure regulated atrio-ventricular delay involves recording atrial activation and ventricle activation, identifying a maximum diastolic pressure, identifying a declination pressure, calculating a percent decrease, and adjusting atio-ventricular delay. The declination pressure occurs at the beginning of an isovolumetric contraction. The percent decrease is calculated between the maximum diastolic pressure and the declination pressure. The atrio-ventricular delay is adjusted according to the percent decrease between the maximum diastolic pressure and the declination pressure.

DETAILED DESCRIPTION OF THE INVENTION

Figure 1:
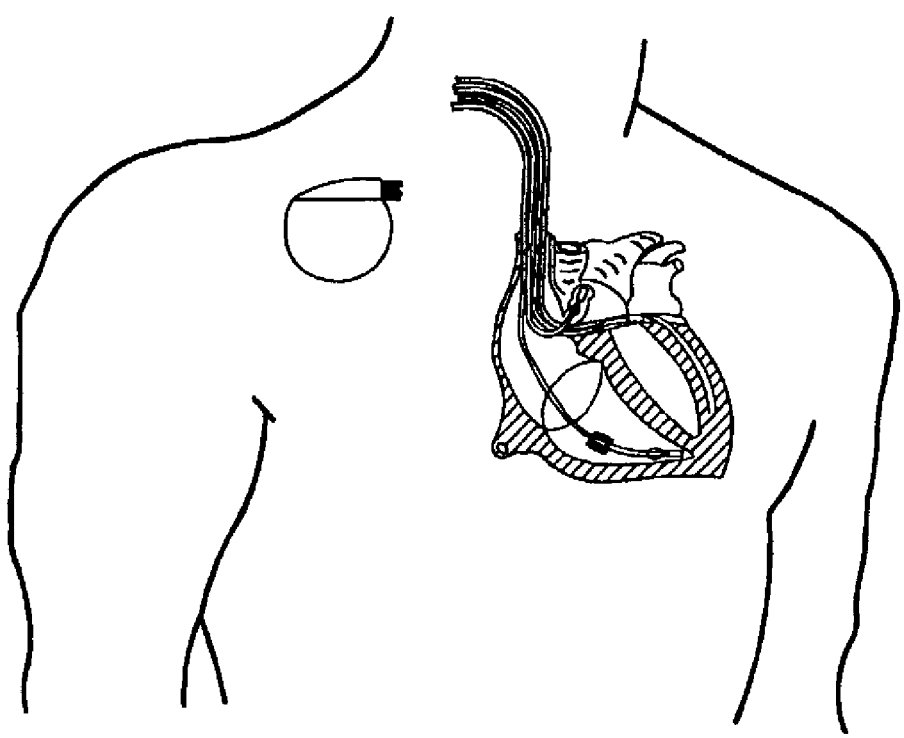
FIG. 1 shows an environmental view of an implantable cardiac device (ICD).
Figure 2:
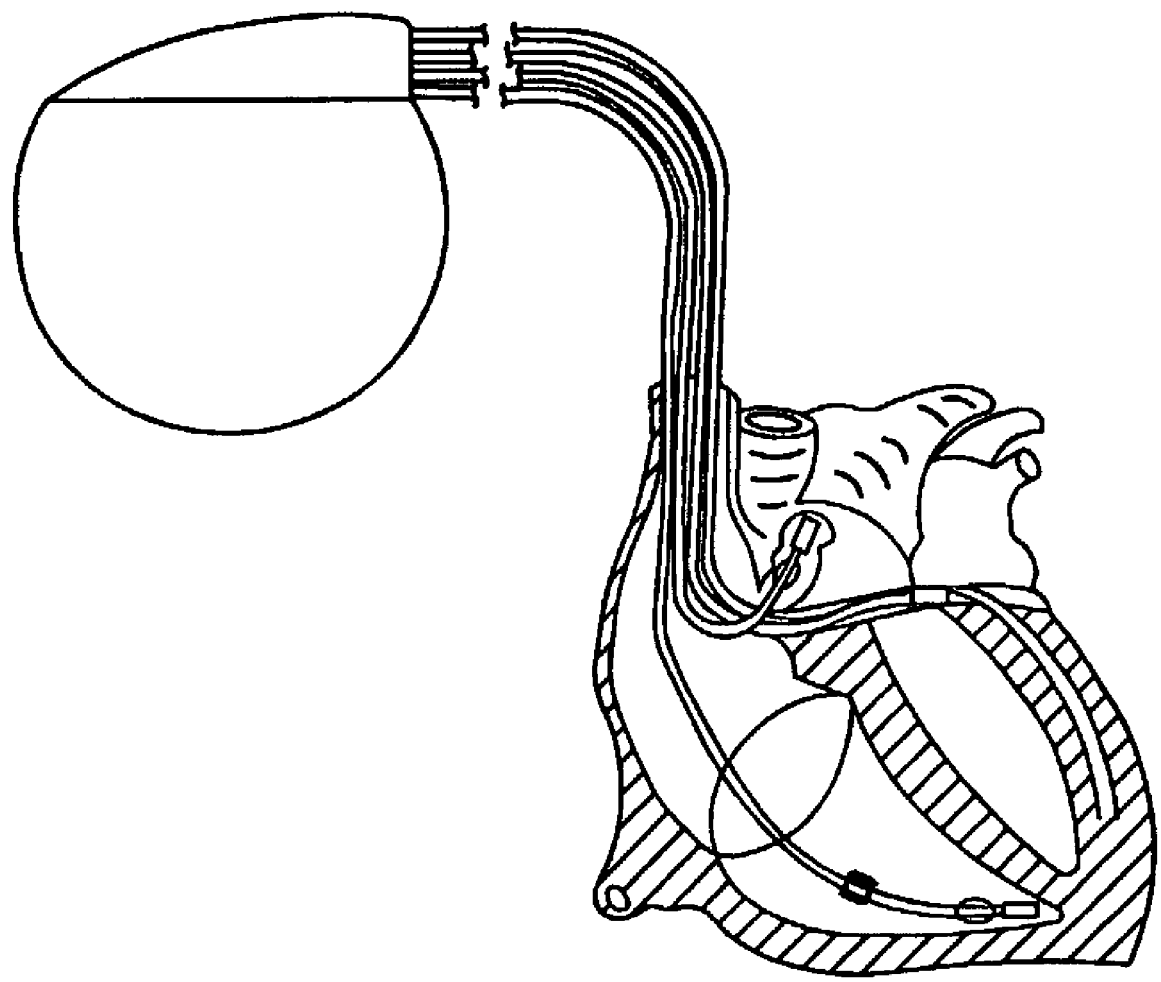
FIG. 2 shows a more detailed environmental view of an ICD.

FIGS. 1 and 2 show an environmental view of an Implantable Cardiac Device (ICD) for optimal intra-left ventricular resynchronization. The ICD can be any ICD capable pacing both the right ventricle and the left ventricle known as bi-ventricular pacing. Implantable Cardiac Devices suitable for bi-ventricular pacing include certain pacemakers, cardioverters, and defibrillators configured for bi-ventricular pacing. For example, the ICD and be an InSync® III Model 8040 pacemaker or an InSync® Marquis cardioverter/defibrillator using leads using two standard right heart electrical leads (in the right atrium and right ventricle) and one left-heart electrical lead such as an Attain™ Model 2187, 2188 or 4193 also available from Medtronic, Inc. in Minneapolis, Minn. USA. The electrical leads are typically implanted transvenously via the coronary sinus and positioned in a cardiac vein to pace the left ventricle.

Figure 3:
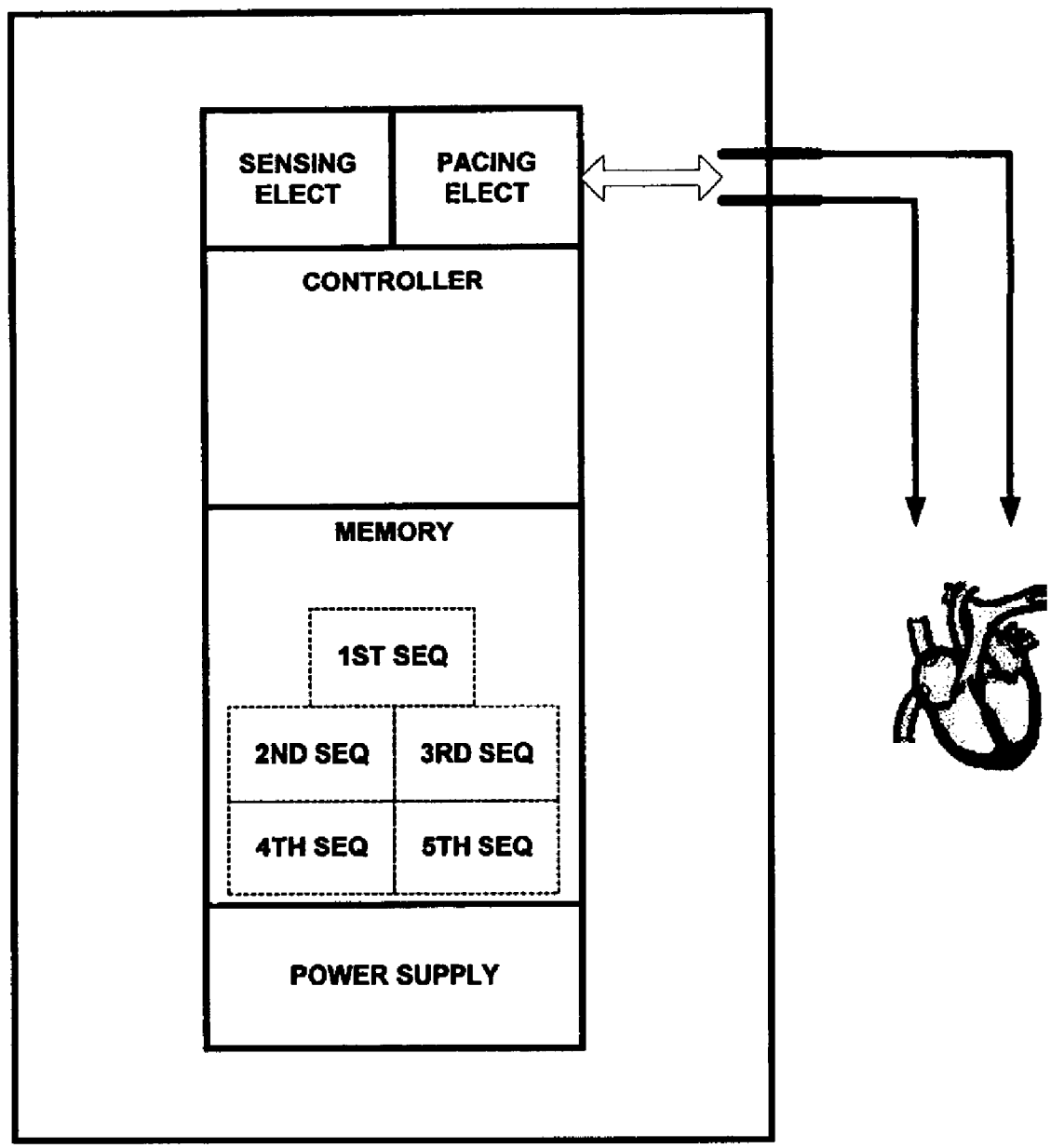
FIG. 3 shows a simplified block diagram of an ICD embodiment.

FIG. 3 shows a block diagram of an implantable cardiac device for optimal intra-left ventricular resynchronization. The cardiac pacemaker comprising a housing, a controller, memory, pacing electronics, sensing electronics, a first electrical lead, a second electrical lead, and software. The housing has a power supply carried in the housing and a feedthrough. The controller is carried in the housing and coupled to the power supply. Memory is coupled to the controller. The pacing electronics are coupled to the controller and the feedthrough. The sensing electronics coupled to the controller and the feedthrough.

The first electrical lead is coupled to the feedthrough and configured for positioning in the right ventricle. The first electrical lead has at least a first electrode for pacing the right ventricle, and the first electrical lead can also have additional electrodes for functions such as pacing the right atrium. The first electrode can also serve as a sensing electrode to provide sensing signals of right ventrical timing to the sensing electronics.

The second electrical lead coupled to the feedthrough and configured for positioning in the left ventricle. The second electrical lead has at least a second electrode for pacing the left ventricle, and the second electrical lead can also have additional electrodes for functions such as pacing the left atrium. The second electrode can also serve as a sensing electrode to provide sensing signals of left ventrical timing to the sensing electronics.

The pressure sensor is placed within the right-ventricle, equivalent as used with Implantable Hemodynamic Monitor or Pressure Sensor Brady Pacemaker, will allow real-time pressure monitoring of the total right ventricle. Four specific pressure points can be monitored and hence the sequence of right-ventricle pressure fluctuations can be used to regulate the required atrio-ventricular delay timing.

Ventricular Election and Ventricular Filling Periods. Following ventricular sense or ventricular paced events, maximal (systolic) pressure is measured followed by minimal (end systolic) acute drop in ventricular pressure. Early diastolic phase begins and mitral flow and tricuspid flow gradually start to fill both ventricles as seen via rapid filling period (E wave) and is finally completed via the active filling period (A wave) or atrial kick.

Atrial sensing occures typically following the E wave and atrial contraction occurs resulting in maximal pressure increase when peak diastolic pressure is obtained. Immediately following, the maximal diastolic pressure starts to decrease until the start of the isovolumetric contraction (IVC) period. After a short IVC, the onset of the ventricular contraction betgins and the ventricular ejection occurs.

Detection. Maximal pressure following atrial sense or atrial pace event depicts peak ventricular filling or peak atrial kick pressure during diastolic period. The percent decrease between peak pressure points and declination pressure point determines the moment of atrio-ventricular delay and can be programmed selected as percent of declination. Example of algorithm: 10 mmHg to 7.5 mmHg=a 25% decrease per time interval of 120 ms.

AV Delay Timing. In the example presented, bi-ventricular pacing spiking occurs at 120 ms after peak diastolic pressure of 10 mmHg decreases 25% to 7.5 mmHg marking moment of atrio-ventricular delay timing. Specific timing algorithms can be defined to accommodate for rest and exercise heart rates and percent decrease per time.

Wedge Pressure. In addition, the Pulmonary Capillary Wedge Pressure (PCWP) is by far the most important pressure indices in heart failure patients and their hemodynamics. Through the use of the pressure sensor, PCWP pressure can be estimated from the on-line, 10 Hz sample frequency of right-ventricle pressure measurements, derived by point of maximal dP/dT. The calculated Wedge Pressure (PCWP) can separately be used to regulate the required pacing heart reate, or aid additional fine atrio-ventricular delay tuning when combined with absolute right-ventricle diastolic pressure indicies.

Figure 4:
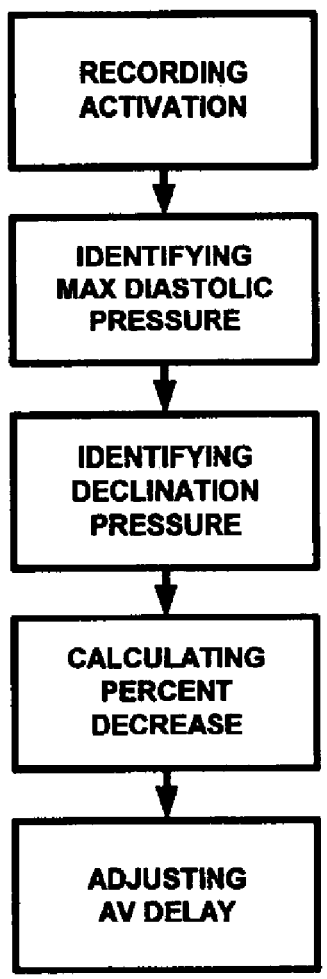
FIG. 4 shows a flowchart of a method for pressure regulated atrio-ventricular delay in multi-site pacing embodiment.

FIG. 4 shows a flowchart of a method for pressure regulated atrio-ventricular delay in multi-site pacing embodiment. The method comprises recording atrial activation and ventricle activation, identifying a maximum diastolic pressure, identifying a declination pressure, calculating a percent decrease, and adjusting atrio-ventricular delay. The declination pressure occurs at the beginning of an isovolumetric contraction. The percent decrease is calculated between the maximum diastolic pressure and the declination pressure. The atrio-ventricular delay is adjusted according to the percent decrease between the maximum diastolic pressure and the declination pressure.

Figure 5:
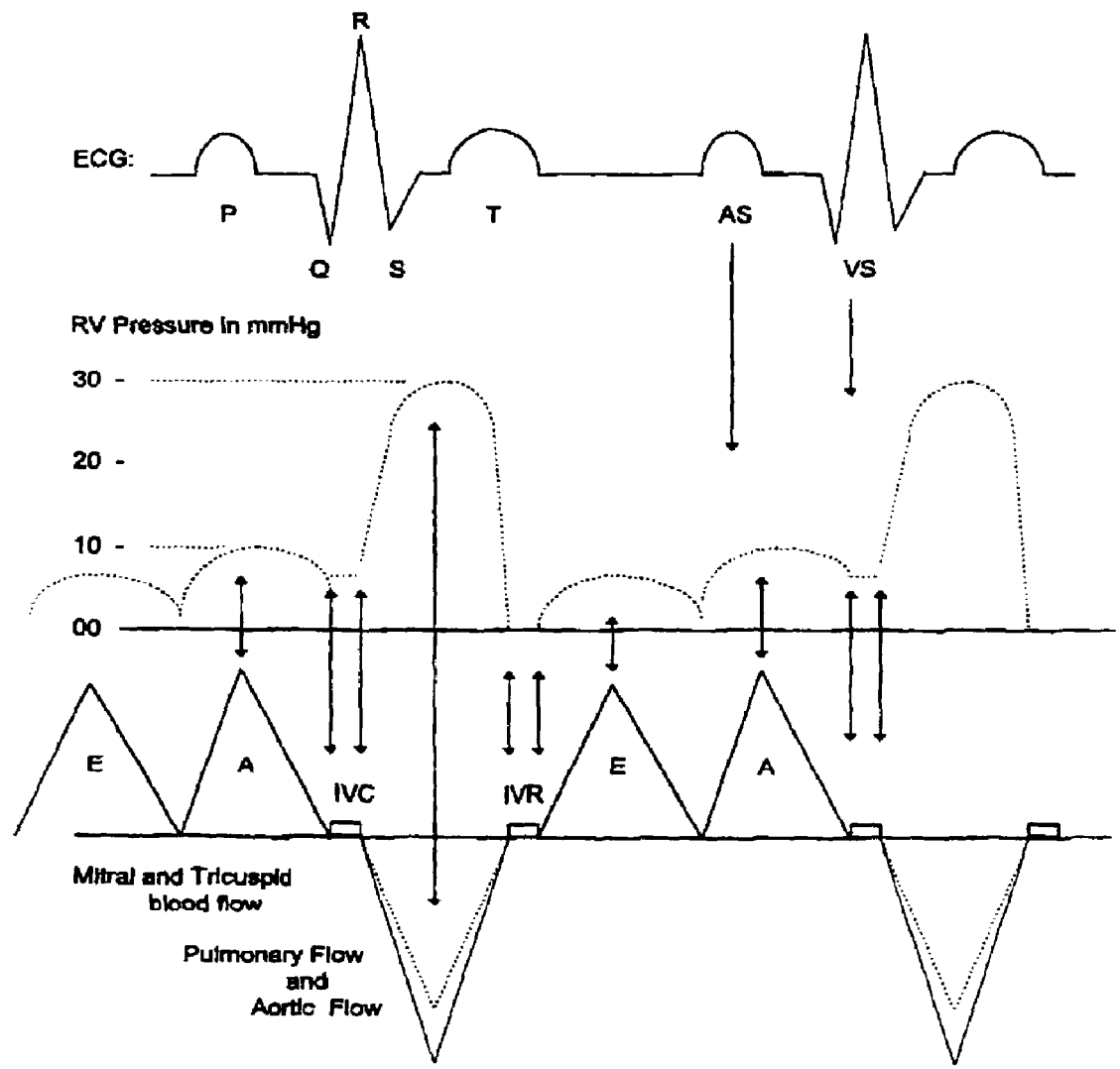
FIG. 5 shows a timing diagram of a patient's heart with proper atrio-ventricular timing that includes an ECG trace, a right-ventricle pressure trace, and blood flow trace.

FIG. 5 shows a timing diagram of a patient's heart with proper atrio-ventricular timing that includes an ECG trace, a right-ventricle pressure trace, and blood flow trace. The example in FIG. 5 shows the situation in a patient with proper intrinsic atrio-ventricular timing. Maximum separation of diastolic E and A mitral and tricuspid waves forms allow for maximal diastolic filling period of both right-ventricle and left ventricle. Systolic pulmonary flow and aortic flow occur after normal closure of A waves on mitral and tricuspid flow patterns and following a short period of isovolumetric contraction period.

Figure 6:
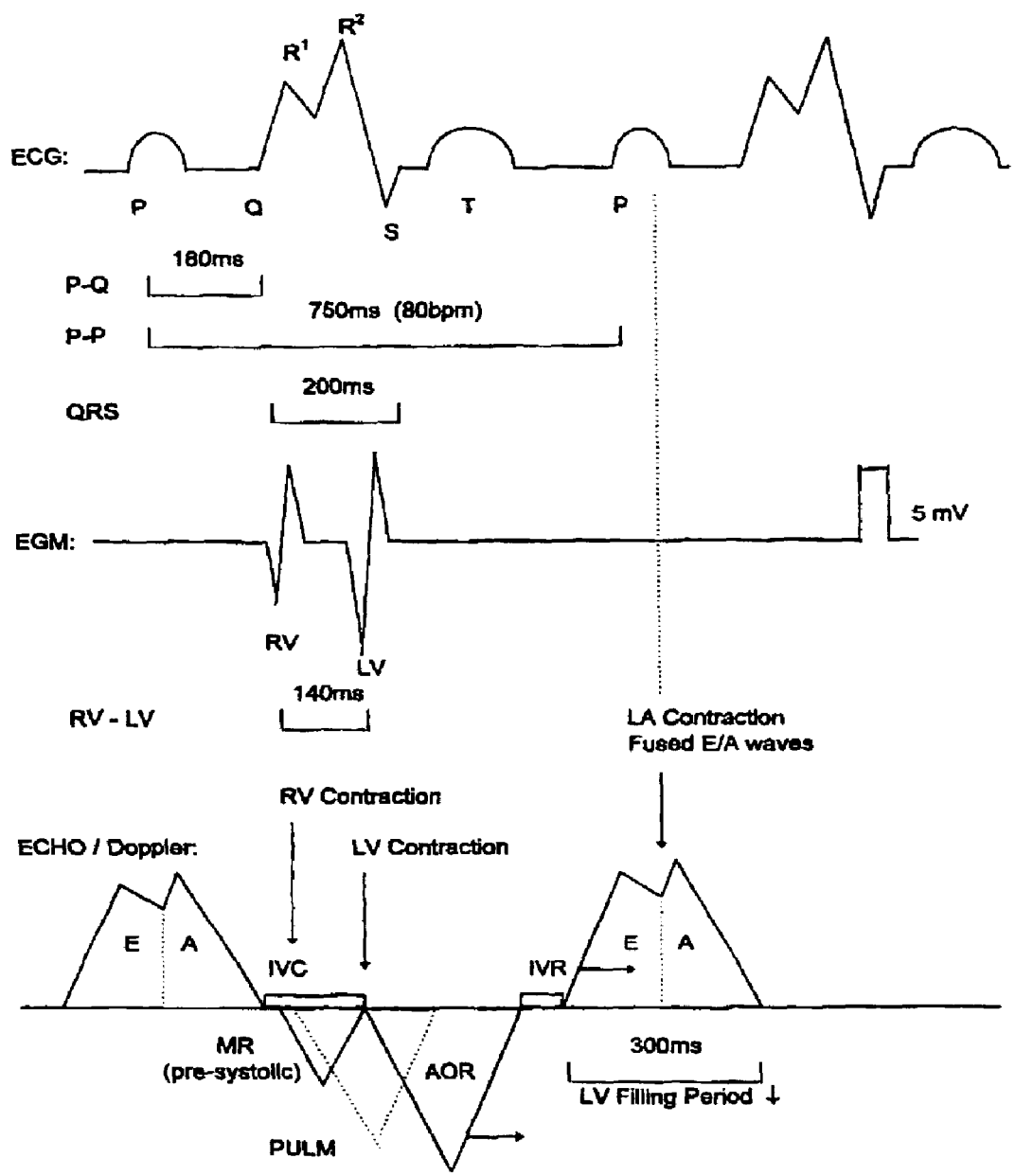
FIG. 6 shows a timing diagram of a patient's heart with dilated cardiomyopathy, left bundle branch block (LBBB) and widened QRS complex that includes an ECG trace, an EGM trace, mitral valve flow trace, aortic flow trace, and cardiac cycle timing intervals.

FIG. 6 shows a timing diagram of a patient's heart with dilated cardiomyopathy, left bundle branch block (LBBB) and widened QRS complex that includes an ECG trace, an EGM trace, mitral valve flow trace, aortic flow trace, and cardiac cycle timing intervals. The example in FIG. 6 the patient has a P-Q interval that is prolonged, and left-ventricle contraction that is greatly delayed resulting in major asynchrony to right-ventricle contraction. In addition, diastolic filling is greatly affected through fusion of E waves and A waves and a greatly reduced left-ventricle filling period through delayed left-ventricle contraction and relaxation (right side shift).

Figure 7:
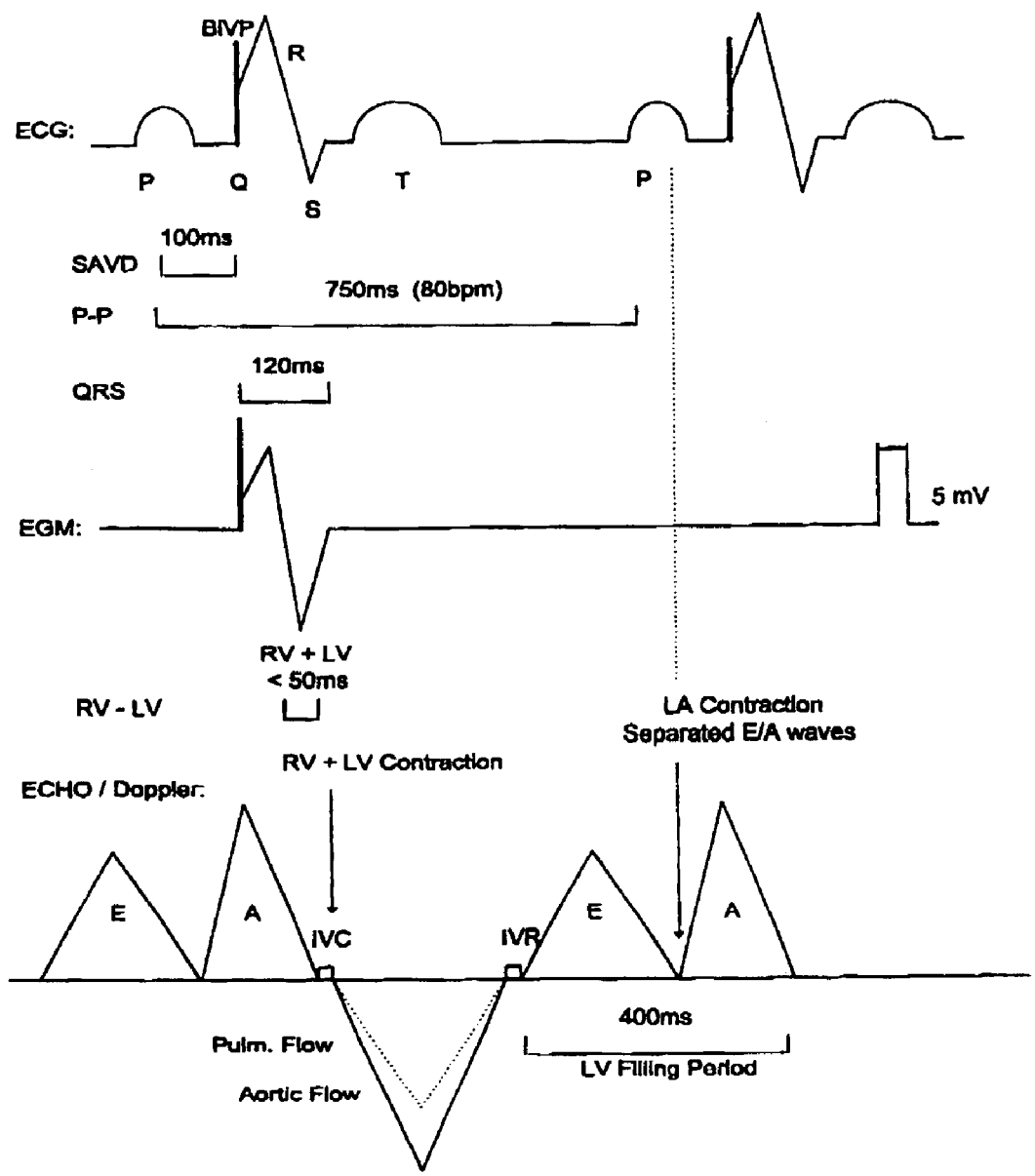
FIG. 7 shows a timing diagram of resynchronized ventricles using shortened atrio-bi-ventricular pacing with optimized pressure regulated atrio-ventricular delay in a patient's heart with dilated cardiomyopathy, left bundle branch block (LBBB) and widened QRS complex that includes an ECG trace, an EGM trace, mitral valve flow trace, aortic flow trace, and cardiac cycle timing intervals embodiment.

FIG. 7 shows a timing diagram of resynchronized ventricles using shortened atrio-bi-ventricular pacing with optimized pressure regulated atrio-ventricular delay in a patient's heart with dilated cardiomyopathy, left bundle branch block (LBBB) and widened QRS complex that includes an ECG trace, an EGM trace, mitral valve flow trace, aortic flow trace, and cardiac cycle timing intervals embodiment.

Figure 8:
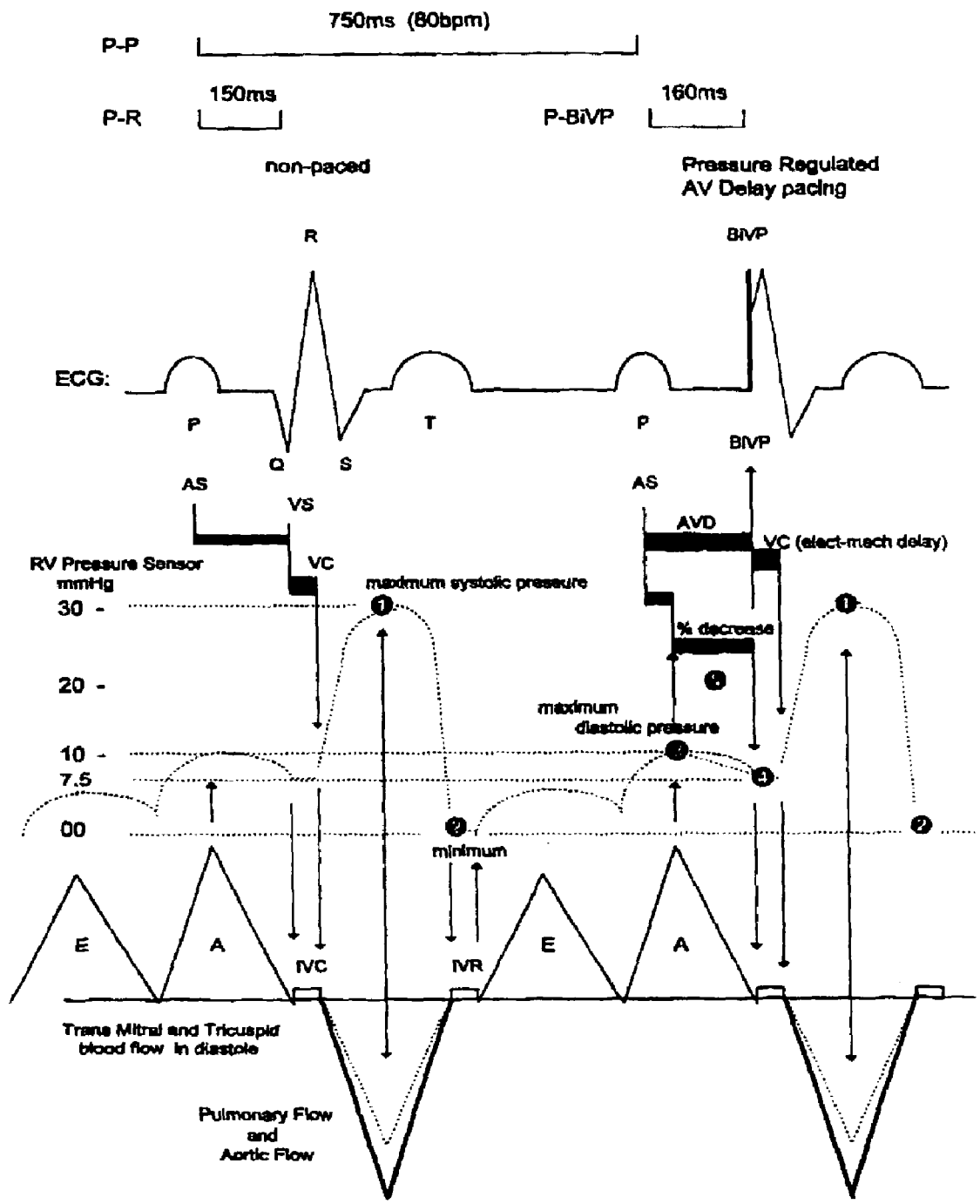
FIG. 8 shows a timing diagram of resynchronized ventricles in a heart with dilated cardiomyopathy, left bundle branch block (LBBB) and widened QRS complex that includes an ECG trace, an EGM trace, mitral valve flow trace, aortic flow trace, and cardiac cycle timing intervals embodiment.

FIG. 8 shows a timing diagram of resynchronized ventricles in a heart with dilated cardiomyopathy, left bundle branch block (LBBB) and widened QRS complex that includes an ECG trace, an EGM trace, mitral valve flow trace, aortic flow trace, and cardiac cycle timing intervals embodiment.

Thus, embodiments of the pressure regulated atrio-ventricular delay for multi-site pacing are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A cardiac pacemaker for pressure regulated atrio-ventricular delay for multi-site pacing, comprising:
   a housing having a power supply carried in the housing and a feedthrough;
   a controller carried in the housing coupled to the power supply;
   memory coupled to the controller;
   pacing electronics coupled to the controller and the feedthrough;
   sensing electronics coupled to the controller and the feedthrough;
   a first electrical lead coupled to the feedthrough and configured for positioning in an atrium;
   a second electrical lead coupled to the feedthrough and configured for positioning in a ventricle a pressure sensor carried on the third electrical lead;
   a second electrical lead coupled to the feedthrough and configured for positioning in the left ventricle; and,
   software stored in memory containing instructions including,
      a first sequence of instructions when executed by the controller, causes the controller to record atrial activation and ventricle activation,
      a second sequence of instructions when executed by the controller, causes the controller to identify a maximum diastolic pressure, a third sequence of instructions when executed by the controller, causes the controller to identify a declination pressure occurring at an isovolumetric contraction beginning, a fourth sequence of instructions when executed by the controller, causes the controller to calculate the percent decrease between the maximum diastolic pressure and the declination pressure, and, a fifth sequence of instructions when executed by the controller, causes the controller to adjust atrio-ventricular delay according to the percent decrease between the maximum diastolic pressure and the declination pressure.

2. A method for pressure regulated atrio-ventricular delay in multi-site pacing, comprising:

recording atrial activation and ventricle activation, identifying a maximum diastolic pressure, identifying a declination pressure occurring at an isovolumetric contraction beginning, calculating a percent decrease between the maximum diastolic pressure and the declination pressure, and, adjusting atrio-ventricular delay according to the percent decrease between the maximum diastolic pressure and the declination pressure.

\* \* \* \* \*